(12) United States Patent
Chelbi Alix et al.

(10) Patent No.: US 8,394,422 B2
(45) Date of Patent: Mar. 12, 2013

(54) ARSENIC THERAPY FOR AUTOIMMUNE AND/OR INFLAMMATORY DISEASES IN MICE AND HUMANS

(75) Inventors: Kmar Chelbi Alix, Paris (FR); Pedro Bobé, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 12/480,299

(22) Filed: Jun. 8, 2009

(65) Prior Publication Data
US 2009/0297624 A1 Dec. 3, 2009

Related U.S. Application Data

(60) Continuation-in-part of application No. 12/244,732, filed on Oct. 2, 2008, which is a division of application No. 10/512,430, filed as application No. PCT/FR03/01314 on Apr. 25, 2003, now abandoned.

(30) Foreign Application Priority Data

Apr. 26, 2002 (FR) ...................................... 02 05276

(51) Int. Cl.
*A01N 59/22* (2006.01)
*A01N 55/02* (2006.01)
*A61K 31/285* (2006.01)

(52) U.S. Cl. ........................................ 424/623; 514/504
(58) Field of Classification Search .................. 424/623; 514/504
See application file for complete search history.

(56) References Cited

U.S. PATENT DOCUMENTS

| | | | |
|---|---|---|---|
| 5,550,153 A | 8/1996 | Kerz | |
| 5,889,048 A * | 3/1999 | Vorobieva | 514/496 |
| 6,191,123 B1 | 2/2001 | Uckun et al. | |
| 6,333,028 B1 | 12/2001 | Berd | |
| 6,733,792 B1 | 5/2004 | Lu et al. | |
| 2002/0183385 A1* | 12/2002 | Ellison et al. | 514/504 |
| 2004/0022869 A1 | 2/2004 | Chen et al. | |
| 2009/0098216 A1* | 4/2009 | Chelbi Alix et al. | 424/623 |

FOREIGN PATENT DOCUMENTS

| | | |
|---|---|---|
| EP | 0 804 928 | 11/1997 |
| EP | 955 052 | 11/1999 |
| FR | 2 539 993 | 8/1984 |
| FR | 2 572 730 | 5/1986 |
| FR | 2 782 010 | 2/2000 |
| WO | WO94/21249 | 9/1994 |
| WO | WO-95/01789 | 1/1995 |
| WO | WO-99/18798 | 4/1999 |
| WO | WO-99/24029 | 5/1999 |
| WO | WO-99/55344 | 11/1999 |
| WO | WO-00/07616 | 2/2000 |

OTHER PUBLICATIONS

Nathan, Nature, 2002, 420, 846-852.*
The Merck Manual, obtained online at : www.merck.com,Chapter 126a, downloaded on: Apr. 19, 2011.*
The Merck Manual, obtained online at: www.merck.com, search terms inflammatin, downloaded on Apr. 19, 2011.*
The Merck Manual, obtained oline at: www.merck.com, chapter 185, downloaded on Apr. 19, 2011.*
www.sustainablefuture.se, obtained online at: www.sustainablefuture.se/arsenic/diseases.html, downloaded on Apr. 13, 2011.*
Feng et al., J. N. Bethune Univ Med. Sci., 2000, 260-262.*
The Merck Manual, obtained online at www.merckmanuals.com, Chapters 186, 86 and 70, downloaded on: Apr. 19, 2011.*
Harrison et al., International Immunopharmacology, 2001, 1, 647-656.*
National Institutes of Health, Patient Information Publications, obtained online at: http://www.cc.nih.gov/ccc/patient_education/pepubs/gvh.pdf, downloaded on May 7, 2012.*
Huang et al.; "Environmental and Molecular Mutagensis"; 1995; 25, 188-196.
Office Action issued Jan. 24, 2008, U.S. Appl. No. 10/512,430, 11 pages.
Office Action issued Jun. 12, 2008, in U.S. Appl. No. 10/512,430, 15 pages.
International Search Report issued Oct. 7, 2003; International Application No. PCT/FR03/01314.
Bobe et al., "Nitric Oxide Mediation of Active Immunosuppression Associated with Graft-Versus-Host Reaction," *Blood*, vol. 94, pp. 1028-1037 (1999).
Burkhart et al., "Xenobiotic immunosuppressive agents: therapeutic effects in animal models of autoimmune diseases," *Rheumatology International*, 1997, pp. 85-90, vol. 17, No. 3, XP002224717.

* cited by examiner

*Primary Examiner* — Abigail Fisher
(74) *Attorney, Agent, or Firm* — Foley & Lardner LLP

(57) ABSTRACT

The invention relates to a method for treating and/or preventing autoimmune and/or inflammatory diseases, including the graft-versus-host disease, comprising administering to a patient in need thereof, a therapeutically effective amount of an arsenic compound or a pharmaceutically acceptable salt thereof.

1 Claim, 12 Drawing Sheets

MRL/lpr control  MRL/lpr treated

ARSENIC THERAPY FOR AUTOIMMUNE AND/OR INFLAMMATORY DISEASES IN MICE AND HUMANS

The invention relates to the use of arsenic for treating and/or preventing autoimmune and/or inflammatory diseases such as autoimmune lympho-proliferative syndrome; chronic inflammatory diseases, especially chronic inflammatory diseases of the intestine such as Crohn's disease; and graft-versus-host disease.

The use of arsenic is already known for treating different types of cancers: leukemia, lymphoma, ovarian cancer, lung cancer.

Such treatments are described in documents FR 2 782 010, U.S. Pat. No. 6,333,028, FR 2 539 993, U.S. Pat. No. 6,191,123, EP 955 052, WO 99/24029, WO 99/18798 and WO 99/55344.

The use of arsenic for treating other diseases such as coccidioses, parasitic diseases, dermatomycoses or chronic asthenia syndrome is also known. These treatments are in particular described in documents FR 2 572 730, U.S. Pat. No. 5,550,153, WO 94/21249 and WO 95/01789.

However, the use of arsenic for treating autoimmune diseases is to date not known.

The term "autoimmunity" is intended to mean a state of immunization of an individual against itself. Autoimmune diseases are diseases of the immune system characterized by the production of antibodies (called autoantibodies) which react with antigens (called autoantigens) originating from the tissues of the actual patient (for review, see Schwartz et al (1984)). The most common autoimmune diseases are: systemic lupus erythematosus, acute disseminated lupus erythematosus, uveitis, Bechet's disease, sarcoidosis, Sjögren's syndrome, rheumatoid arthritis, juvenile arthritis, Fiessinger-Leroy-Reiter syndrome, gout, osteoarthrosis, polymyositis, myocarditis, primary biliary cirrhosis, Crohn's disease, ulcerative colitis, multiple sclerosis and other demyelinating diseases, aplastic anemia, essential thrombocytopenic purpura, any disease associated with a nontumoral lymphoproliferation, B-lymphocyte lymphoma, Simmonds' syndrome, Basedow-Graves disease and Graves' opthalmopathy, subacute thyroiditis and Hashimoto's disease, Addison's disease, chronic hepatitis, insulin-dependent diabetes mellitus (type 1).

The medicinal products of the prior art that are used for treating autoimmune diseases, in particular systemic diseases, generally result in a nonspecific general suppression of the immune system. Most commonly, these medicinal products do not distinguish between the pathological immune response and a protective immune response of the organism. Thus, immunosuppressive medicinal products (for example: corticosteroid, azathioprine, cyclophosphamide and cyclosporine) are often administered in order to suppress the proliferation of autoreactive lymphocytes. Anti-inflammatory medicinal products are often prescribed for patients suffering from rheumatoid arthritis. Globally, these medicinal products have harmful side effects, the suppression of the immune response resulting in risk of infection and of cancer.

Insofar as the prior art is extremely rich in candidate substances capable of acting against such diseases, it is very difficult to pinpoint substances that are actually active in vivo and capable of treating autoimmune diseases.

The invention aims to overcome the drawbacks of the prior art by proposing effective compounds for the treatment and/or prevention of autoimmune and/or inflammatory diseases, with very reduced or completely absent unwanted side effects.

To this end, a subject of the invention, according to a first aspect, is the use of an arsenic compound for preparing a medicinal product for treating autoimmune and/or inflammatory diseases.

In particular, the abovementioned chosen diseases will be targeted.

Preferably, autoimmune diseases belonging to certain categories of metabolic disorder will be targeted, such as:
- a deficiency in maintaining lymphoid organ homeostasis, of the ALPS type;
- a deficiency in maintaining liver homeostasis (hepatomegaly);
- cutaneous diseases (lupus, psoriasis, etc.);
- a defective apoptosis of proliferating cells of the liver, of the skin;
- a defective apoptosis of proliferating cells of the immune system which can result, inter alia, in an overexpression of FasL (autoimmune chronic hepatitis, etc.) or an abnormal production of cytokines (rheumatoid arthritis, insulin-dependent (autoimmune) diabetes mellitus, etc.).

The products of the present invention can also be used for treating graft-versus-host (GVH) disease.

Bone marrow transplantation has greatly expanded as a clinical treatment modality for several disorders of hematopoiesis and certain hematological malignancies. The GVH reaction is a major complication of bone marrow transplantation. The immunopathophysiology of GVH reaction is complex and is considered to involve an inductive and an effector phase. In the inductive phase, GVH reaction is initiated by mature alloreactive T cells of donor origin, specific for antigenic differences that can be encoded by genes located outside the major histocompatibility complex (MHC). This may occur both in man, when donor and recipient are HLA compatible, and in mice, when donor and recipient bear the same H-2 haplotype. The development of the GVH disease is associated with an active immunosuppression inducing a severe immunodeficiency syndrome responsible for much of the mortality (Bobé et al., Blood 1999, 94, 1028-37). In the effector phase, inflammatory reactions may develop in specific host target tissues such as skin, liver, and gastrointestinal tract that are characterized by mononuclear cell infiltration and histopathological damage. Conventional means for treating GVH disease remain insufficient. Current treatment of chronic GVH disease with corticosteroids alone or with added agents such as calcineurin inhibitors (cyclosporin or tacrolimus) or sirolimus (rapamycin) has a very high failure and complication rate, and new treatment approaches are needed for both primary and salvage therapy. Indeed, if the GVH disease is severe and requires intense immunosuppression involving steroids and additional agents to get under control, the patient may develop severe infections as a result of the immunosuppression and may die of infection. The products of the present invention are thus highly useful for preventing and/or overcoming these problems and complications.

According to preferred embodiments, the diseases to be treated are autoimmune lymphoproliferative syndrome (ALPS), lupus erythematosus, rheumatoid arthritis, Sjögren's syndrome, autoimmune chronic hepatitis and insulin-dependent diabetes mellitus.

According to other preferred embodiments, the diseases to be treated are chronic inflammatory diseases, especially chronic diseases of intestine (CDI), usually regarded as inflammatory diseases, including Crohn's disease, ulcerative colitis and undetermined inflammatory colitis.

According to yet another preferred embodiment, the disease to be treated is the GVH reaction.

In the present application, the term "arsenic" or "arsenic compound" or "arsenic derivative" will be used. This term is not limited to only the examples described; it encompasses the various forms of arsenic which have a preventive or curative effect on the target pathologies. In this sense, the present application describes in vivo tests which make it possible to screen for effective compounds, which exhibit biological activity results of at least 10, 20, 50, 80, 90, 100, 150, 200% of those obtained in the detailed description which follows using the arsenic $As_2O_3$.

Those skilled in the art having available to them these tests can therefore, without excessive effort, identify arsenic compounds that are therefore therapeutically effective in the context of the invention. Preference will in particular be given to an arsenic compound chosen from: $As_2O_3$, $As_2O_5$, $AS_4O_6$, $As_2S_2$, $As_2S_3$, $As_2S_5$ and $As_4S_4$, most particularly $As_2O_3$. The candidate arsenic compounds can be preselected using suitable in vitro tests before being tested in vivo.

These arsenic compounds can be screened in order to measure their therapeutic effectiveness by means of an in vivo screening method comprising the administration of a candidate arsenic compound to animals suffering from an autoimmune and/or inflammatory disease, typically at a daily dose of the order of 5 to 10 mg/kg of bodyweight.

According to another aspect, the invention relates to a pharmaceutical composition intended for the treatment and/or prevention of at least one autoimmune and/or inflammatory disease, characterized in that it comprises an effective amount of an arsenic compound or a pharmaceutically acceptable salt of this compound. This effective amount intended to be administered daily is a dose of 3 to 10 mg/kg of bodyweight, preferably 5 to 10 mg/kg.

This composition may also comprise a pharmaceutically acceptable transporter or excipient. Depending on the applications, it will be in a form that is suitable for any appropriate route of administration, e.g., oral, parenteral, intraperitoneal administration.

The term "pharmaceutically acceptable salt" refers to salts prepared from pharmaceutically acceptable nontoxic acids and bases, including inorganic and organic acids and bases. Use may in particular be made of an acid salt of sodium or of potassium, or an arsenic iodide.

Moreover, the invention relates to the use of compounds other than arsenic, but capable, just like arsenic, of inhibiting phosphatase activities, for treating autoimmune and/or inflammatory diseases.

The transporter may be of very varied type, according to the form of the preparation used for the administration, in particular oral or parenteral (lozenge, capsule, powder, intravenous injection, infusion).

For oral administration, the pharmaceutical preparation may be in liquid form, for example in solution, in the form of a syrup or of a suspension, or in the form of a powder intended to be redissolved. Such a liquid preparation can be prepared according to suitable techniques with pharmaceutically acceptable excipients such as suspending agents (for example: sorbitol, cellulose derivatives), emulsifiers (for example: lecithin or acacia), nonaqueous transporters (for example: fractionated vegetable oil), and preserving agents (for example: sorbic acid).

When solid oral preparations (lozenge, powder, capsule, tablet) are involved, the pharmaceutical compositions are prepared using suitable excipients such as binding agents (corn starch, polyvinyl pyrrolidone, hydroxypropylmethylcellulose), filling agents (lactose, microcrystalline cellulose), lubricants (magnesium stearate, talc, silica) or swelling agents (sodium lauryl sulfate).

For administration by inhalation, the compounds are typically included in a preparation of the aerosol type using a suitable gas.

The arsenic derivatives can also be formulated for parenteral administration, for example by continuous or noncontinuous injection. The liquid media are generally similar (water, glycol, oil, buffer) to those used for oral preparations.

The formulations by injection can be provided in the form of dosage units (ampoules, mini-containers) with a suitable protective agent. These compositions to be injected can also be in the form of a suspension, a solution or an emulsion and can contain stabilizers and/or dispersing agents. The active principle can also be prepared in the form of a powder with a suitable transporter. The invention also provides packs or kits comprising at least one container containing the arsenic derivative in a pharmaceutically acceptable form. For example, the arsenic may be in the form of a pharmaceutically acceptable solution, such as a saline solution, a dextrose solution or a sterile buffer solution; the kit may also comprise suitable means for injection, such as a sterile packaged syringe.

The therapeutic dose used in the treatment of autoimmune and/or inflammatory diseases is variable according to the seriousness and the conditions of treatment. The dose, and where appropriate the frequency, are to be adjusted as a function in particular of age and of bodyweight. Given the potential toxicity of the arsenic, the dosage and the duration of the treatment are determined in an appropriate manner, according to the seriousness of the disease and the long-lasting nature, or otherwise, of the recovery, it being possible for the treatment to last from a few days to a few months until complete or at least partial recovery is achieved. The formulation is typically administered daily, for a period of 10 to 50 days. Several successive treatments may be carried out, of the order of one month apart.

In addition, the arsenic may be administered, where appropriate, with other active principles that participate in the treatment of the targeted diseases. Thus, mention may be made of the use of the arsenic in combination with corticosteroids such as prednisone or drugs such as methotrexate, for treating autoimmune syndromes and/or chronic inflammatory pathologies.

According to another aspect, the invention relates to a method for treating, in particular in humans, autoimmune and/or inflammatory diseases including the GVH disease comprising the administration to the patient of a pharmaceutically effective amount of an arsenic derivative. The invention relates to a method of treatment comprising the administration of 5 to 10 mg of arsenic per kilogram of bodyweight per day. The administration may be oral, parenteral, intraperitoneal, or via any other appropriate route.

The effect of the treatment with the arsenic compounds on the autoimmune and/or inflammatory diseases studied can be monitored by means of suitable techniques as described in the examples hereinafter, in particular measuring the weight of the organs (nodes, spleen, etc.), studying the structure of the tissues (external study, anatomopathology).

The term "method of treatment" is intended to mean a curative or preventive treatment. The inventors have demonstrated the efficacy of the arsenic compounds for preventing the appearance of autoimmune and/or inflammatory diseases, as is described in the examples below.

Other subjects and advantages of the invention will emerge on reading the detailed description illustrated by means of the drawings in which.

Figure 10:
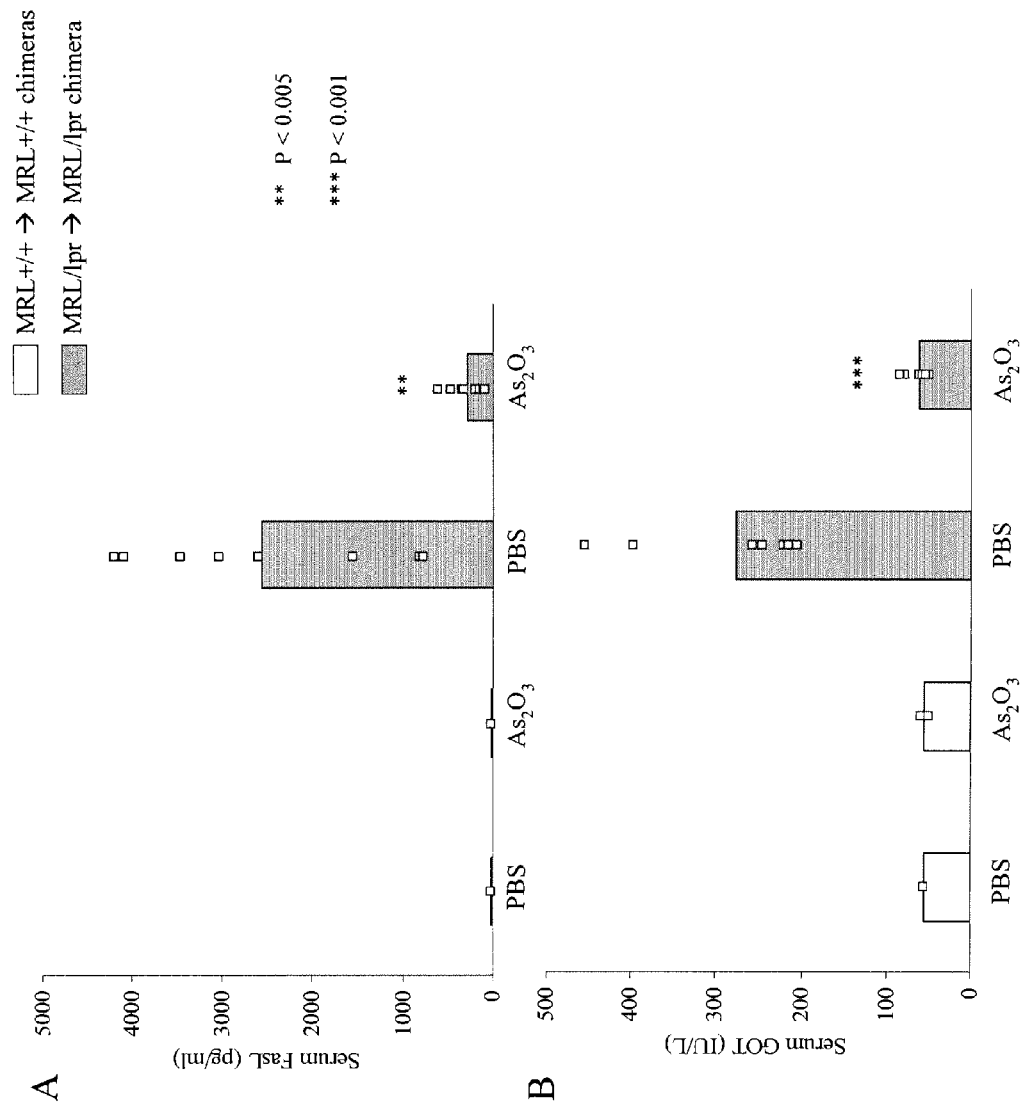

FIGS. 10 A and B illustrate the effect of $As_2O_3$ on FasL (FIG. 10A) or GOT (FIG. 10B) levels in MRL/lpr→MRL+/+ chimeras.

Figure 11:
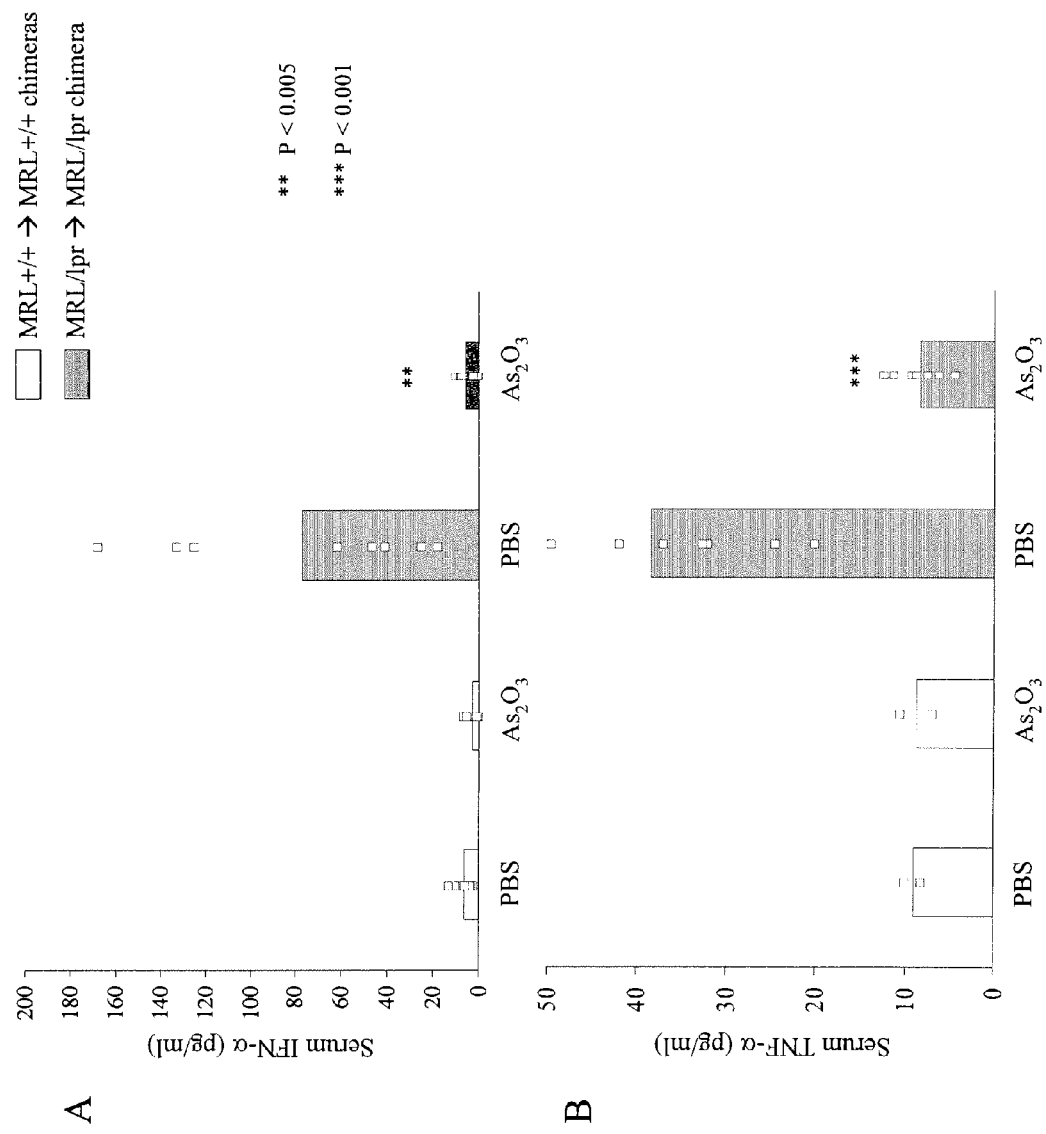

FIGS. 11A and B illustrate the reduction of IFN-α (FIG. 11A) and TNF-α (FIG. 11B) syntheses in $As_2O_3$-treated MRL/lpr mice.

Figure 12:
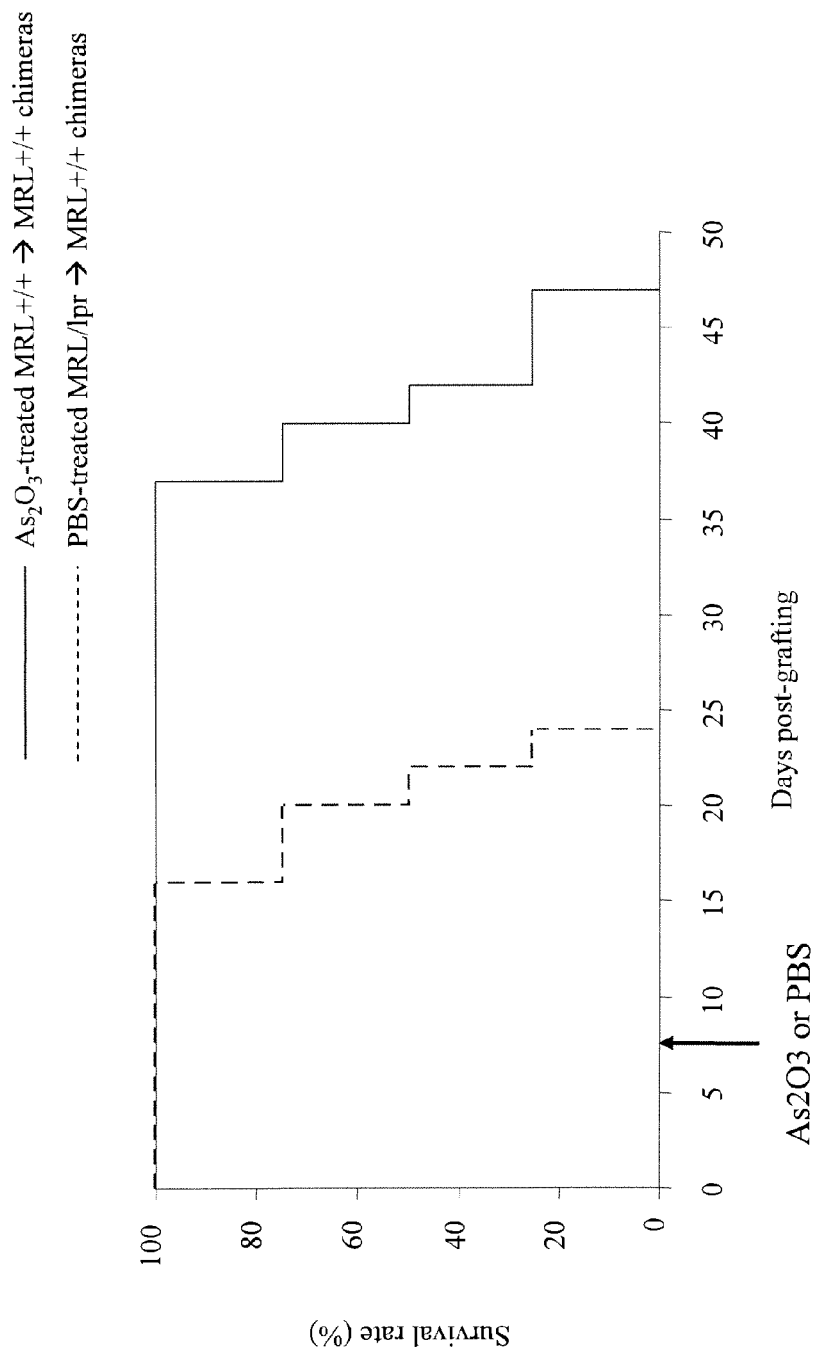

FIG. 12 illustrates the survival of MRL/lpr→MRL+/+ chimeras treated by $As_2O_3$.

EXAMPLES

Part I

Examples Using the MRL/lpr Mouse as a Model of Autoimmune Pathologies

The inventors have studied mice referred to as MRL mice homozygous for the lpr mutation (MRL/lpr). Lymphoproliferation (lpr) results in an accumulation of activated T lymphocytes, of phenotype $CD4^+CD8^-$ or $CD4^-CD8^+$ which have escaped the process of negative regulation via the apoptotic pathway. Thus, in MRL/lpr mice, hypertrophy of lymph nodes occurs, the mass of which is 100 times greater than that of the lymph nodes of MRL+/+ mice, which are congenic for the lpr gene, and a spleen whose size is multiplied by 7 and a thymus whose weight, at the 22nd week, is double that of the MRL+/+ mice are observed. These activated T lymphocytes which accumulate will gradually repress the expression of their CD4 or CD8 receptors and become double-negative T lymphocytes having the phenotype: $TCR\alpha\beta CD4^-CD8^-B220^+$, which will be responsible for the lymphoproliferation.

I.1 The MRL/lpr Mouse is a Spontaneous Model of Autoimmune Pathologies

The MRL/lpr mouse is in particular a spontaneous model of autoimmune diseases such as disseminated lupus erythematosus with the presence of erythematous lesions of the skin and of rheumatoid arthritis. This animal also exhibits Sjögren's syndrome characterized by the destruction of the salivary and lachrymal glands subsequent to an infiltration of lymphoid cells. These mice produce, as they age, a large quantity of autoantibodies which are responsible for a lethal glomerulonephritis due to immunocomplex deposits in the glomeruli of the kidney. Thus, the lifespan of the MRL/lpr mouse is considerably shortened compared with that of the MRL+/+ mouse: ~4-5 months in the MRL/lpr mouse compared with ~2 years in the MRL+/+ mouse. The congenic MRL+/+ mouse develops an attenuated form of glomerulonephritis but does not exhibit any lymphoproliferation; thus, the lpr mutation is thought to act as an accelerating factor in the occurrence of the lupus-related syndrome.

I.2 Arsenic Therapy for the Pathologies in the MRL/lpr Mouse

Initially, the inventors determined the optimum dose of arsenic ($As_2O_3$) to be injected into the MRL/lpr mice. Two concentrations were chosen: 1 and 5 μg of $As_2O_3$/g of mouse. At date T0, these injections were given daily. After one week of treatment, the group receiving the highest dose showed spectacular signs of improvement of the lupus-specific skin lesions, which was not the case for the mice treated at the lowest dose. Knowing that the MRL/lpr autoimmune mice die, on average, after 4 to 5 months, compared with the normal MRL+/+ mice which die after ~2 years, the inventors decided to conserve, for the subsequent treatments, only the dose of 5 μg/g of mice. The control MRL+/+ mice having received this dose of arsenic exhibit, at T0+5 months, no sign of treatment-related pathologies.

From the end of the first week of treatment, the inventors formed 5 groups of animals:
 1st group, aimed at the curative treatment of an already present pathology,
 2nd group, aimed at preventing the appearance of pathologies,
 3rd group, aimed at determining the lifespan of the treated animals,
 4th group, aimed at determining the dose effect,
 5th group, aimed at evaluating the effect of stopping the treatment.

Each of the five groups has its controls consisting in injecting the dilution buffer for the arsenic. In addition, the animals present in the control and treated groups are derived from the same litter, which makes it possible to obtain reliable comparisons. At T0+5 months, more than 60 mice (MRL/lpr and MRL+/+) are undergoing treatment.

Results for Group 1

This study is aimed at the curative treatment of an already present pathology.

A) Study of Skin Lesions

Figure 1:
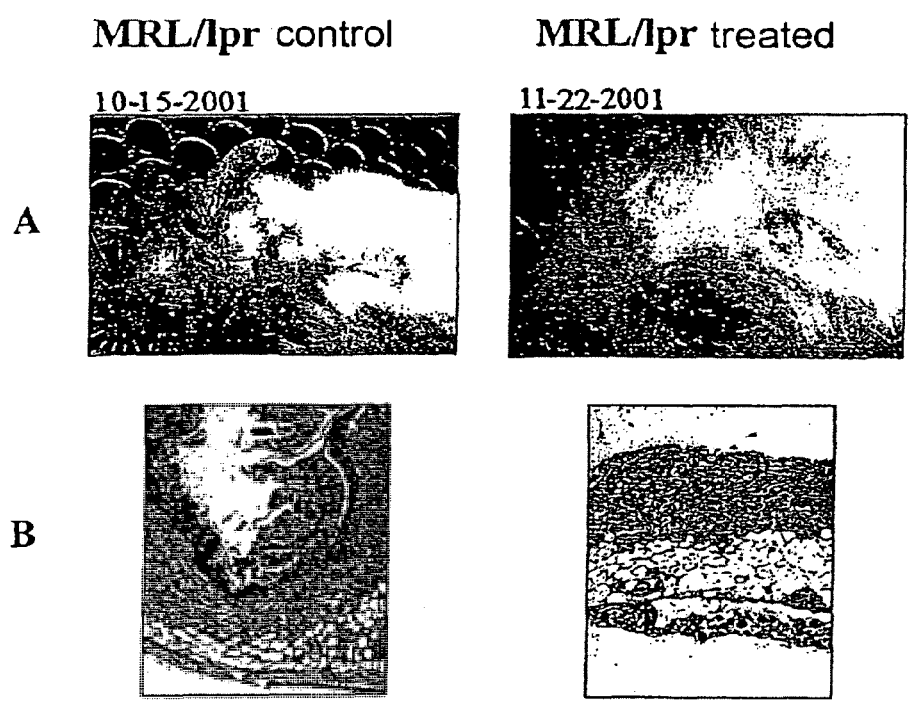
FIGS. 1A and 1B show the recovery obtained by means of the arsenic on MRL/lpr mice, respectively the external morphology and the study of the skin of the neck by anatomopathology.
Figure 2:
FIG. 2 shows the effect of the arsenic on MRL/lpr mice; on the left, untreated mouse with exophthalmia; on the right, treated mouse which has completely recovered.
Figure 2:
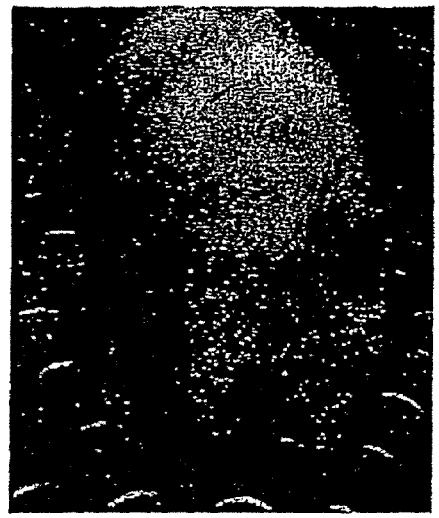

As early as the end of the first month of treatment, the MRL/lpr mice showed a complete disappearance of the lupus-related skin lesions (FIG. 1) and a spectacular decrease in the exophthalmia characteristic of the pathology of the MRL/lpr mouse (FIG. 2). From this date, other treated and nontreated groups were formed and the groups treated with the $As_2O_3$ systematically showed a disappearance of the exophthalmia and of the skin problems. In addition, by means of anatomopathological studies of the skin (FIG. 1B), complete disappearance of the pathological tissue was confirmed in the MRL/lpr mice treated with the $As_2O_3$, but not in the control MRL/lpr animals. This arsenic treatment is therefore effective for treating the skin lesions related to an autoimmune pathology such as lupus.

In parallel with these studies on the skin, other organs that are targets for autoimmune pathologies, such as the kidney, the lung, the liver, the eye, etc., were removed and analyzed by anatomopathology. In addition, these various organs, along with the spleen, the lymph nodes and the thymus, were weighed. The results are given in table 1. In summary, the arsenic treatment returns the following organs to a normal weight, comparable to that of the organs of the MRL++ mouse: lymph nodes, spleen and liver. It should be noted that the action of this agent is targeted to the lymphoid organs and the liver, in the knowledge that the MRL/lpr mouse exhibits anomalies of lymphoid organ and liver homeostasis.

Figure 6:
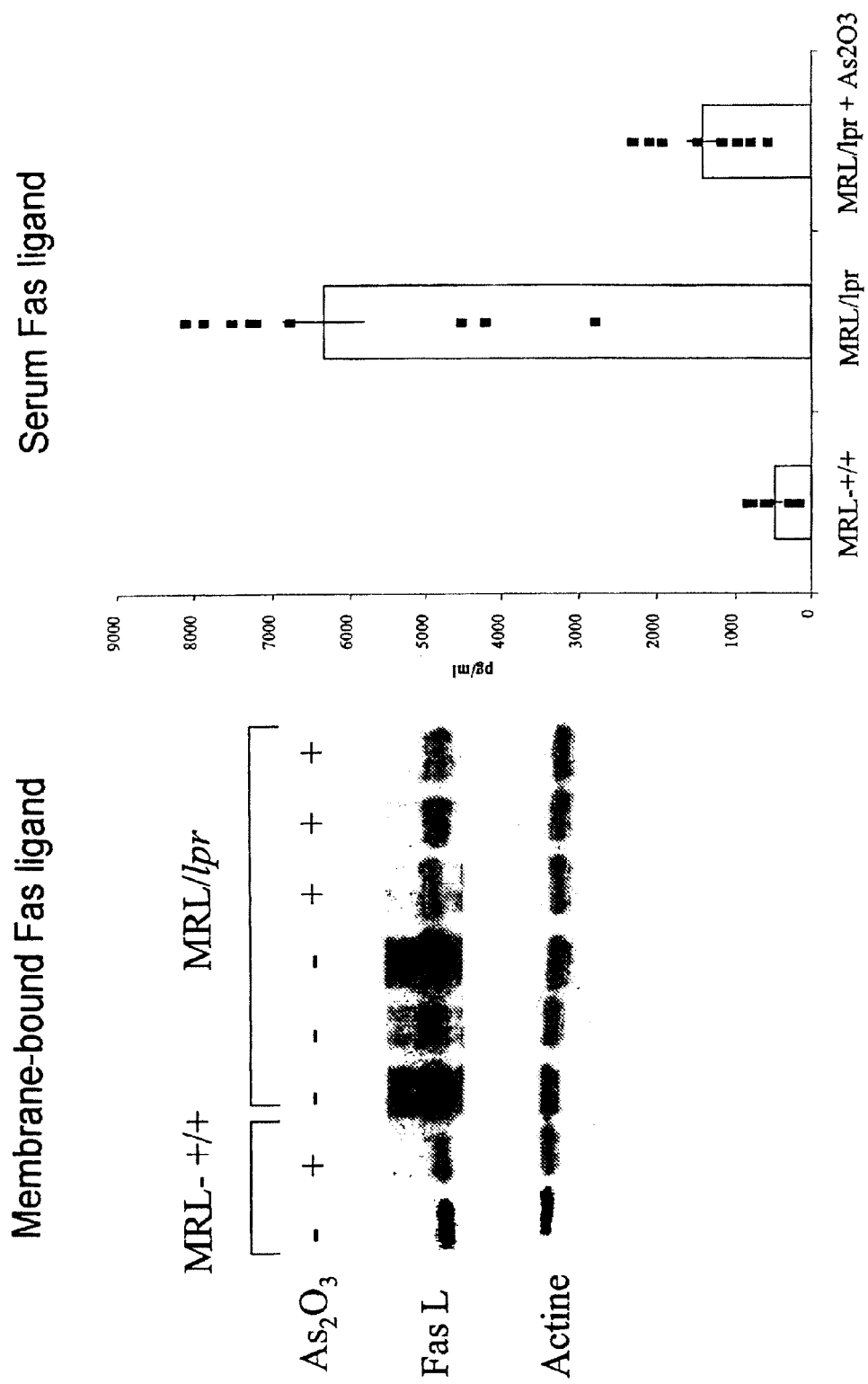
FIG. 6 show the decrease in the amount of cytokines and in the amount of membrane-bound FasL due to the arsenic.

FasL (FIG. 6) is related to the elimination of the activated T lymphocytes which are responsible for the lymphoproliferation.

In addition, disseminated lupus erythematosus and rheumatoid arthritis are characterized by the presence of high titers of serum autoantibodies. In the autoimmune MRL/lpr mice, these autoantibodies accumulate in the kidney in the form of immunocomplexes (FIG. 7, control B, arrows) and are responsible for glomerulonephritis which results in the

TABLE 1

| | Organ weight in grams | | | | | | | |
|---|---|---|---|---|---|---|---|---|
| | MRL+/+ control | MRL+/+ Arsenic | MRL+/+ Arsenic | MRL/lpr control | MRL/lpr Arsenic | MRL/lpr Arsenic | MRL/lpr *treatment stopped | MRL/lpr *treatment stopped |
| Axillary nodes | 0.01 | 0.01 | 0.01 | 0.38 | 0.01 | 0.02 | 0.38 | 0.15 |
| Mesenteric nodes | 0.03 | 0.05 | 0.03 | 2.61 | 0.05 | 0.05 | 1.97 | 1.03 |
| Spleen | 0.09 | 0.10 | 0.15 | 0.53 | 0.13 | 0.17 | 0.41 | 0.20 |
| Liver | 2.46 | 2.40 | 2.45 | 3.30 | 2.58 | 2.89 | 3.21 | 3.12 |
| 2 lungs | 0.35 | 0.32 | 0.30 | 0.69 | 0.33 | 0.40 | 0.51 | 0.50 |
| Kidney | 0.47 | 0.44 | 0.44 | 0.44 | 0.52 | 0.53 | 0.55 | 0.55 |
| Heart | 0.21 | 0.22 | 0.22 | 0.29 | 0.20 | 0.25 | 0.29 | 0.26 |

Figure 3:
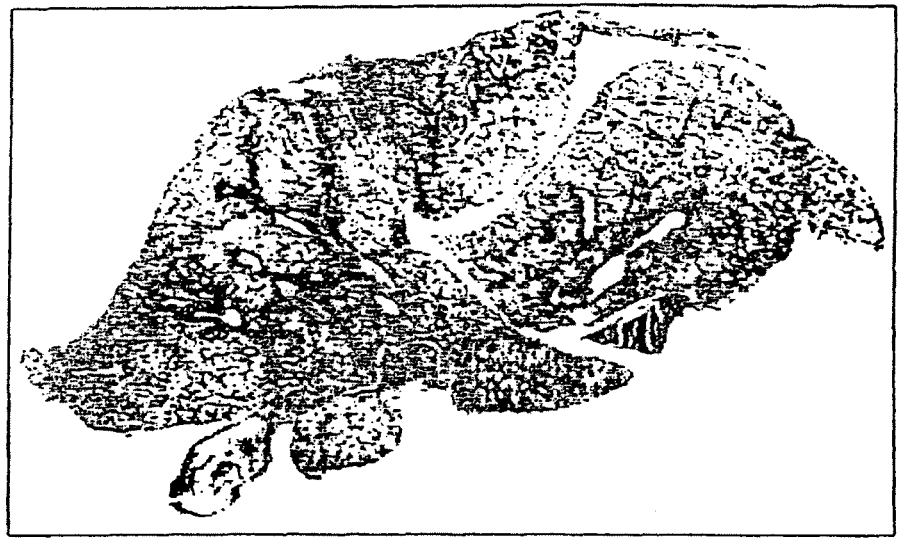
FIG. 3 show sections of pulmonary tissue with substantial infiltrations by lymphoid cells around the vessels and bronchioles (control), and a normal pulmonary architecture (arsenic)
Figure 3:

*Treatment stopped: MRL/lpr mouse treated with arsenic for two months
Treatment then stopped for a period of two months before sacrificing the animal In addition, it should be noted that, in severe forms of disseminated lupus erythematosus, the patients exhibit a considerable inflammation of the lung with substantial infiltrations by lymphoid cells. The autoimmune MRL/lpr mice exhibit the same symptoms with, around the vessels and the bronchioles, substantial infiltrations by lymphoid cells (FIG. 3A, control). On the other hand, the mice treated with $As_2O_3$ have a normal pulmonary architecture with only a few lymphoid cells around the vessels and none around the bronchioles (FIG. 3A, arsenic).

B) Study of the Lymphoproliferation

Figure 4:
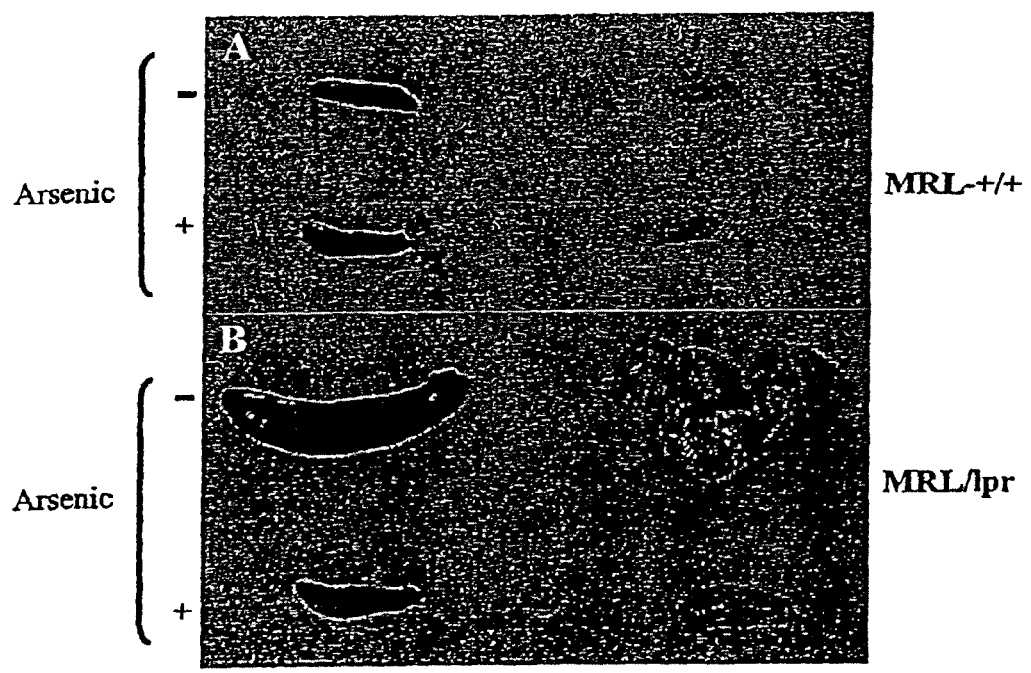
FIGS. 4A and 4B illustrate the return to normal anatomy of the internal organs due to the treatment with arsenic.
Figure 5:
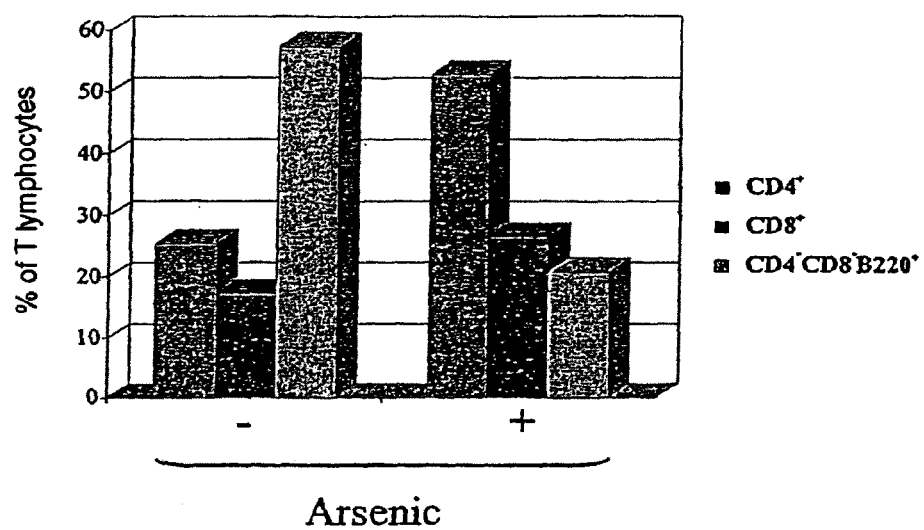
FIG. 5 represents the decrease in the percentage of CD4-CD8-B220+ T lymphocytes due to the arsenic.

After 1 month and 20 days of treatment, a group of 3 control MRL/lpr mice and a group of 3 treated MRL/lpr mice were sacrificed in order to evaluate the effectiveness of the treatment on the lympho-proliferation. The organs analyzed were the thymus, the spleen and the lymph nodes. FIG. 4 illustrates the spectacular decrease in the size of the spleen and of that of one of the mesenteric nodes. The phenotype of the lymphoid populations present in this spleen and this node was determined by flow cytometry. In summary, the arsenic treatment induces a disappearance of the lymphoproliferation due to the virtually complete elimination of the population of double-negative T lymphocytes, of phenotype TCRαβCD4⁻CD8⁻B220⁺, responsible for the lymphoproliferation. In addition, this cell population of abnormal phenotype is replaced with T lymphocytes of normal phenotype CD4⁺CD8⁻ and CD4⁻CD8⁺ (FIG. 5). However, the level of reduction of the number of these double-negative T cells depends on the duration of the treatment. Thus, a treatment of three months makes it possible to eliminate all the double-negative T cells.

Figure 7:
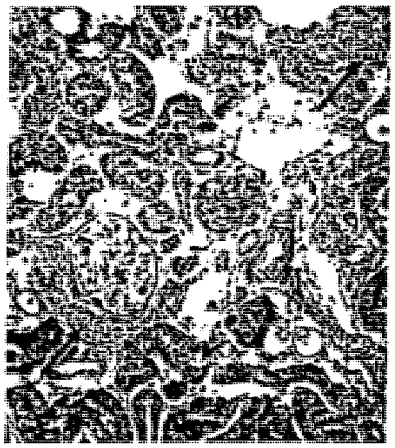
FIG. 7 show the decrease, due to the arsenic, in the amount of autoantibodies in the form of immunocomplexes, accumulated in the kidney, and the infiltration of the kidney by cells of the immune system in the animals not treated with the arsenic.
Figure 7:
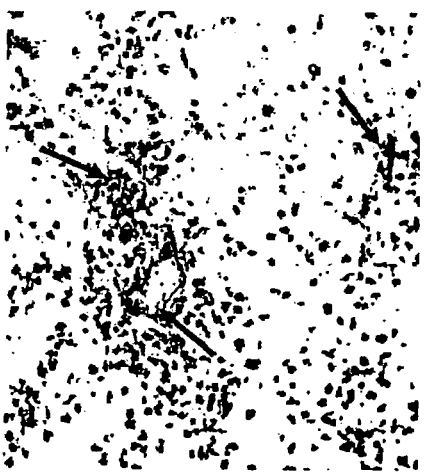

In addition, the autoimmune MRL/lpr mice exhibit a high production of pro-inflammatory cytokines and of death cytokines such as alpha-IFN and gamma-IFN, IL-18, TNF-alpha and soluble FasL, unlike the normal MRL+/+ mice. Treatment of these autoimmune MRL/lpr mice with arsenic returns the amount of cytokines to a normal level, like that observed in the normal MRL+/+ mice. This decrease in the amount of cytokines and in the amount of soluble membrane death of the mice in 4 to 5 months. Treatment of the MRL/lpr mice with arsenic decreases by 60 to 70% the autoantibody titer (anti-double-stranded DNA IgG). This decrease in the autoantibody titer results in an absence of immunocomplexes in the kidney (FIG. 7, arsenic B), a significant reduction in the glomerulonephritis, and an increase in survival. In addition, the mice treated with arsenic do not shown any infiltration of the kidney by cells of the immune system (FIG. 7, arsenic A) compared with the untreated animals (FIG. 7, control A, arrows).

Figure 8:
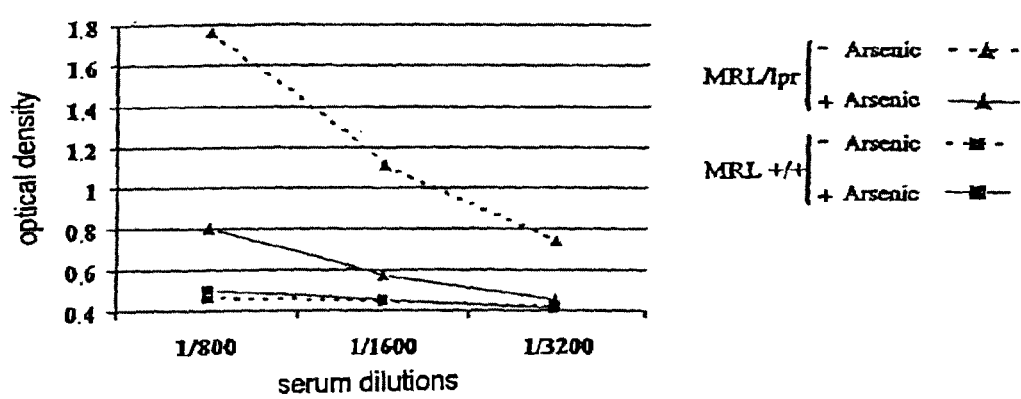
FIG. 8 illustrates the disappearance of the abnormal titer of anti-DNA antibodies due to the arsenic: the anti-DNA antibodies are a characteristic of lupus in humans and MRL/lpr mice.

In conclusion, all the results obtained with group 1 show that arsenic is an effective treatment for eliminating the activated T lymphocytes responsible in the MRL/lpr mouse for the autoimmune lympho-proliferative syndrome (FIG. 8). In fact, arsenic is effective for treating the disseminated lupus erythematosus-related skin lesions in the MRL/lpr mouse. Arsenic is also an effective treatment for reducing the amount of cytokines in the MRL/lpr mouse, and also for treating the glomerulonephritis in the MRL/lpr mouse by reducing the autoantibody titer.

C) Study of the Evolution of Glucose Levels

5-Month-old female NOD (non obese diabetic) mice, which were developing the first symptoms of diabetes, were treated for 2 months with arsenic. The evolution of the pathology was evaluated by measuring the amount of glucose in the urine. Only the NOD mice treated with arsenic showed a normal glucose level in the urine.

Results for Group 2

This study is aimed at preventing the appearance of the pathologies.

The aim of this group of animals, which was begun at T0, is to evaluate the preventive effect of an arsenic treatment on the development of the lymphoproliferation and of the autoimmune pathologies. To do this, 4 groups of animals 1.5 months old were formed. Two of these groups consist of MRL/lpr mice and the other two groups consist of MRL+/+ mice. One MRL/lpr group and one MRL+/+ group were treated with 5 µg of arsenic per gram of mouse, and the other two control groups were treated with the dilution buffer for the arsenic. At T0+1 month, animals from each group were sacrificed. The organs analyzed were the thymus, the spleen, the lymph nodes, the skin, the liver, the kidney and the heart. A virtually complete absence of the lymphoproliferation was observed in the MRL/lpr mice treated with arsenic; in these animals, the non-lymphoid organs such as the heart or the kidney were not modified by the treatment. The arsenic therefore has a preventive effect on the development of the lymphoproliferation. The phenotype of the lymphoid populations present in this spleen and this node was determined by flow cytometry. As for the results for group 1, the arsenic makes it possible to eliminate the population of double-negative T cells which accumulate as the MRL/lpr mouse ages. In addition, the organs of these treated mice have a normal weight; there is therefore neither the lympho-proliferation nor the hepatomegaly that are observed in the control mice. The liver, the spleen, a lymph node, an eye, etc., were removed in order to be analyzed by anatomopathology.

Results for Group 3

Figure 9:
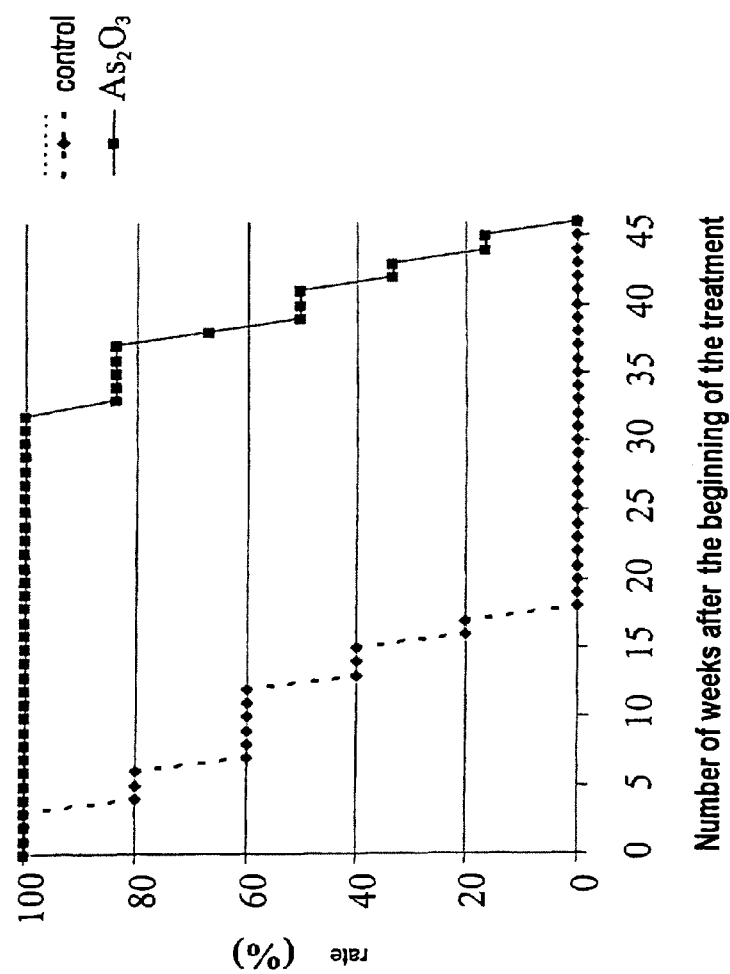
FIG. 9 illustrates the survival of the animals: all the control animals are dead after 4 months, all the treated animals are alive.

This study is aimed at determining the lifespan of the treated animals. This experiment was begun at T0, and very sick MRL/lpr mice were treated either with arsenic or with the dilution buffer for the arsenic. At date T0+14 weeks, 100% of the treated MRL/lpr mice are alive, whereas 100% of the control MRL/lpr mice, which were not treated, are dead. In addition, after 35 weeks of treatment, the MRL/lpr mice are still alive with no signs of lymphoproliferation or of autoimmune pathologies (FIG. 9).

In addition, lethally irradiated MRL+/+ mice had their bone marrow reconstituted with bone marrow from MRL/lpr mice (MRL/lpr→MRL+/+ chimeras) or with bone marrow from MRL+/+ mice (MRL+/+→MRL+/+ chimeras) as a control. After reconstitution, the chimeras are treated with arsenic or are not treated. While 100% of the untreated MRL/lpr→MRL+/+ chimeras died of a graft-versus-host (GvH) reaction two weeks after the transplant, the chimeras treated with arsenic were alive. The arsenic is therefore effective against GvH and makes it possible to spectacularly increase the survival of the animals.

Results for Group 4

This study is aimed at determining the dose effect.

It is desirable to determine very precisely the preventive and curative effect of various doses of arsenic on the evolution of the pathologies developed by the MRL/lpr mice. Five groups of animals (MRL/lpr and MRL+/+) were treated with the following concentrations: 2.5, 5, 7.5, 10 and 15 µg/g of mouse.

The dose of 15 µg/g of mouse proved to be lethal in a few days for the curative treatment. For the preventive treatment, the dose is also very toxic and the animals died after two months. The dose of 2.5 µg/g of mouse is not sufficiently effective for the curative treatment in view of the skin lesions and of the size of the nodes visible from the outside of the animal (and as observed after opening the animal). The concentrations of 5, 7.5 and 10 µg/g result in complete disappearance of skin lesions. The complete curative effect was confirmed on the various organs studied. The lowest effective dose (5 µg/g for the mouse) of arsenic is preferably used in order to avoid any risk of toxicity.

Results for Group 5

This study is aimed at evaluating the effect of the treatment being stopped.

Some of the animals from group 1, for which the skin lesions had completely disappeared and whose sisters that had been sacrificed had shown a complete recovery, had their treatment gradually stopped over two weeks. After the treatment had been stopped for three months, these animals exhibited the skin pathologies characteristic of lupus, and a reappearance of the lymphoproliferation and of the hepatomegaly (table 1). These results indicate that, at least for a homozygous mutation, as in the case of the MRL/lpr mouse, the treatment cannot be definitively stopped. Insofar as the mutation is heterozygous in humans, the possibilities for treatment are increased.

All these results make it possible to confirm the effectiveness of an arsenic therapy for autoimmune diseases in humans. In addition, since those skilled in the art have some knowledge regarding arsenic therapy in humans for a particular form of leukemia, acute promyelocytic leukemia, and now, by virtue of the invention, also regarding the effective doses in mice, its use for the treatment of autoimmune diseases in humans, such as ALPS, does not pose any problems. Furthermore, this treatment is very advantageous since it is not expensive.

Part II

Examples Concerning the GvH Disease

II-1 Materials and Methods:

Hematopoietic chimeras. Spleen and bone marrow cells from MRL/lpr were injected i.v. into MRL+/+ lethally irradiated (1000 cGy) in a $^{137}$Cesium irradiator (MRL/Lpr→MRL+/+ chimeras). The control group consisted of irradiated MRL+/+ grafted with MRL+/+ cells (MRL+/+ →MRL+/+ chimeras). All mice used in this graft protocol were sex matched.

Mice and $As_2O_3$ Treatment.

MRL/Lpr→MRL+/+ and MRL+/+→MRL+/+ chimeras were injected i.p. daily with 2.5, 5, 7.5, 10 or 15 µg/g body weight of As2O3; controls received a daily i.p. injection of PBS (volume weight-determined). Treatments were initiated one week post-grafting.

ELISA Detection of Transaminases.

Blood samples were collected at different times after grafting and glutamic-oxaloacetic transaminase (GOT) and glutamic-pyruvic transaminase (GPT) levels were measured (IU/l).

ELISA Detection of Cytokines.

Serum levels of IFN-α, IFN-γ, soluble FasL, IL-18, TNF-α were assayed using the Mouse Interferon-alpha (PBL Biomedical laboratories, New Jersey, USA), the Mouse Interferon-gamma ELISA Ready-SET-Go (eBioscience, San Diego, Calif.), Mouse Fas Ligand Immunossay (Quantikine M kit; R&D systems, Minneapolis, Minn.), Mouse IL-18 ELISA (R&D Systems), Mouse TNF-α Immunoassay (R&D systems), respectively, following the manufacturer's instructions.

Determination of NO Production.

Serum levels of nitrite were measured using the Nitric Oxide quantification kit (Active Motif, Rixensart, Belgium), according to the manufacturer's instructions (data not shown).

Histopathology and Immunohistochemistry.

Kidney, liver, skin and lung samples were fixed overnight in GlyoFix (Shandon Lipshaw, Pittsburgh, Pa.), then dehydrated, paraffin-embedded and 4-µm-thick sections were cut. After hematoxylin, eosin and saffron staining, sections were examined. For immunohistochemical labeling, kidney samples were frozen in OCT compound, and immune complexes deposited in glomeruli were detected by incubating cryosections with horseradish peroxidase-conjugated goatanti-mouse IgG (1:200, Vector Laboratories, Burlingame, Calif.). Sections were then counterstained with hemalun (work in progress).

II-2 Results:

$As_2O_3$ Returns FasL Levels to Normal in MRL/lpr→MRL+/+ Chimeras

FasL is synthesized by lymphoid cells in membrane-associated and soluble forms. Both forms were studied in MRL/lpr→MRL+/+ and MRL+/+→MRL+/+ chimeras treated with PBS or $As_2O_3$. Cell surface-anchored FasL was analysed by Western blotting on lymphoid cell lysates, while soluble FasL in mouse sera was quantified by ELISA. In MRL/lpr→MRL+/+ chimeras, but not MRL+/+→MRL+/+, both FasL forms were overexpressed. $As_2O_3$ treatment of MRL/lpr→MRL+/+ chimeras sharply decreased soluble and membrane-associated FasL levels to approach those found in $MRL^{+/+}$ mice (FIG. 10A). Transaminase levels (GOT) was also normalised in response to $As_2O_3$ in MRL/lpr→MRL+/+ chimeras mice (FIG. 10B) indicating that $As_2O_3$ is able to cure the GVH-induced hepatitis.

IFN-α and TNF-α Syntheses Decline in $As_2O_3$-Treated MRL/lpr Mice

Cytokine concentrations in the sera were analyzed in MRL/lpr→MRL+/+ and MRL+/+→MRL+/+ chimeras treated with PBS or $As_2O_3$. In MRL+/+→MRL+/+ chimeras, IFN-α and TNF-α syntheses were not affected by $As_2O_3$ treatment (FIGS. 11A, 11B). PBS-treated MRL/lpr→MRL+/+ chimeras had very high serum IFN-α and TNF-α levels but $As_2O_3$ treatment maintained normal cytokine concentrations, comparable to those of MRL+/+→MRL+/+ chimeras (FIGS. 11A, 11B). The level of others inflammatory cytokines and NO highly expressed in In MRL/lpr→MRL+/+ chimeras, but not MRL+/+ was also reduced in response to $As_2O_3$ (data not shown).

$As_2O_3$ Significantly Improves Survival of MRL/lpr→MRL+/+ Chimeras $As_2O_3$ significantly prolonged survival (P<0.001) of male and female MRL/lpr→MRL+/+ chimeras with established GVH reaction (FIG. 12). Indeed, 25 days after grafting, all $As_2O_3$-treated MRL/lpr→MRL+/+ chimeras were alive, whereas all PBS-treated MRL/lpr→MRL+/+ chimeras had died. Therefore, the survival curves of $As_2O_3$-treated MRL/lpr→MRL+/+ chimeras are similar to those of $MRL^{+/+}$→MRL+/+ chimeras.

CONCLUSIONS

The results presented here demonstrate that $As_2O_3$ cure MRL/lpr→MRL+/+ chimeras mice from GVH leading to a significant increased survival. These results show that $As_2O_3$ is a promising therapeutic agent for GVH disease.

The invention claimed is:

1. A method for treating graft-versus-host disease, comprising administering, to a patient in need of such treatment, a therapeutically effective amount of an arsenic compound, wherein the arsenic compound is $As_2O_3$.

* * * * *